United States Patent [19]
Kempin

[11] 4,248,245
[45] Feb. 3, 1981

[54] METHOD AND DEVICE FOR DETERMINING AND SEPARATING THE ALVEOLAR AIR PROPORTION FROM THE BREATHING AIR

[75] Inventor: Hans-Friedhelm Kempin, Lübeck, Fed. Rep. of Germany

[73] Assignee: Drägerwerk Aktiengesellschaft, Fed. Rep. of Germany

[21] Appl. No.: 29,348

[22] Filed: Apr. 12, 1979

[30] Foreign Application Priority Data

Apr. 15, 1978 [DE] Fed. Rep. of Germany ....... 2816499

[51] Int. Cl.³ ............................................. A61B 5/00
[52] U.S. Cl. .................................. 128/719; 128/724; 340/576; 73/421.5 R
[58] Field of Search .............. 128/716, 719, 724, 730; 73/421.5 R; 340/576

[56] References Cited

U.S. PATENT DOCUMENTS

| | | | |
|---|---|---|---|
| 3,613,665 | 10/1971 | Gorsuch | 128/730 |
| 3,831,707 | 8/1974 | Takeuchi | 128/719 X |
| 4,140,106 | 2/1979 | Kirmaier | 128/719 |

*Primary Examiner*—Kyle L. Howell
*Attorney, Agent, or Firm*—McGlew and Tuttle

[57] ABSTRACT

A method of determining and separating the alveolar air proportion of a person's breathing air and thereafter measuring a proportion of a desired gas component thereof, comprises, conveying the exhaled air at a minimum velocity through a conduit, continuously measuring the temperature of the conveyed air, and when the variation in temperature which is measured drops below a predetermined threshold value, directing the exhaled air into a measuring chamber using a sensor device in the measuring chamber to determine the proportion of the desired gas component. A device for this purpose, comprises, a breathing tube which has a passage therethrough for the passage of the breathing air and has a first direct passage terminating in a first outlet to ambience and a second branch passage which passes through a measuring chamber for alveolar air is connected downstream of the measuring chamber to ambience. The device further includes a temperature sensor for continuously sensing the temperature air passing through the passage and for regulating shutoff valves between the passage and the second branch into the measuring chamber in accordance with the temperature sensed so as to separate the alveolar air and direct it into the measuring chamber. In addition, the device includes shutoff valves at the outlets from the measuring chamber and the first branch to ambience which are regulated by the sensing of the temperature and the directing of the sensed value to a comparator which operates on an AND-gate and a timing switch for controlling the operation of the various valves.

5 Claims, 1 Drawing Figure

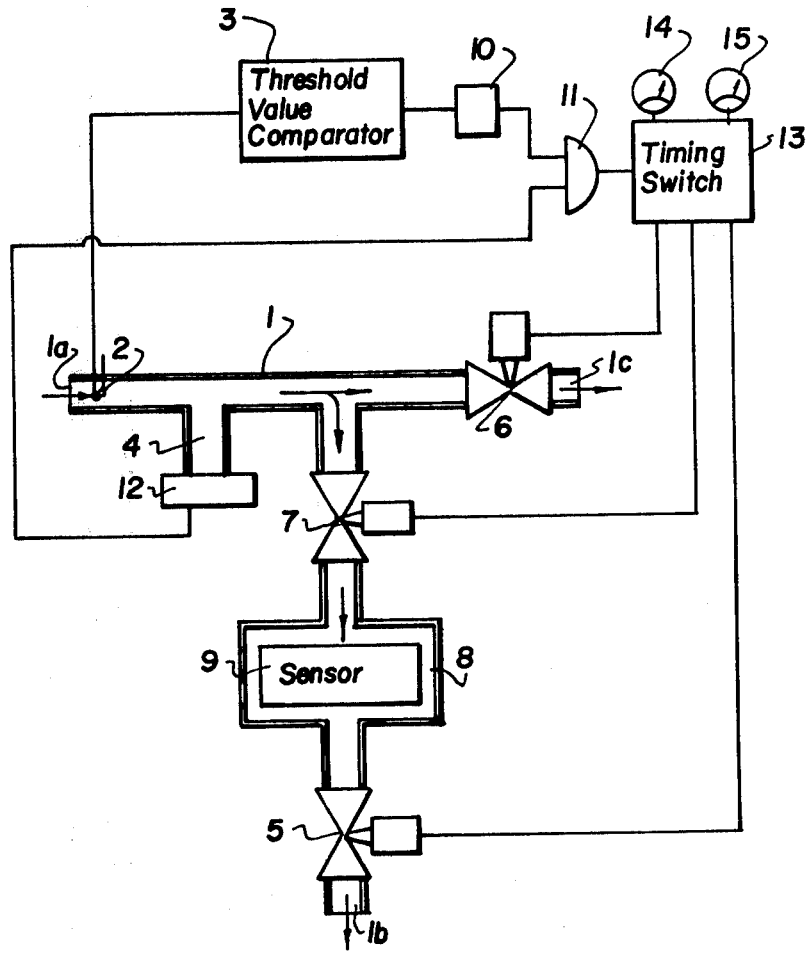

METHOD AND DEVICE FOR DETERMINING AND SEPARATING THE ALVEOLAR AIR PROPORTION FROM THE BREATHING AIR

FIELD AND BACKGROUND OF THE INVENTION

This invention relates to human respiration in general and, in particular, to a method and device for determining and separating the alveolar air proportion from a person's breathing air.

DESCRIPTION OF THE PRIOR ART

The prerequisite for measuring a gas component in the breathing air while determining actual concentration, is that, only that part of the exhaled air is tested for the gas in question, such as $CO_2$, $O_2$ and alcohol which could become equilibrated with this gas in the alveoli of the lungs. Consequently, in terms of the measuring technique, the commuting air from the mouth and throat cavities, as well as the mixed air, is to be separated from the alveolar air.

In a prior art measuring method, the separation of the alveolar air from the mixed and commuting air, necessary for measuring the desired gas component of the breathing air, is effected as soon as the concentration of another gas component which has been continuously followed from the beginning of the measurement reaches a predetermined value. Specifically, it is the $CO_2$ content which is measured prior to measuring the content of alcohol. Starting from the idea that the $CO_2$ is a measure for the $O_2$ exchange in the lungs, a high $CO_2$ content must indicate that breathing air from the lungs, thus alveolar air, is concerned.

Consequently, during the test, the measuring device initially and continuously measures the $CO_2$ of the exhaled air and, upon reaching the predetermined threshold value, which is 4.5% of $CO_2$ in the present example, switches on the alcohol measuring section to measure the alcohol content in the breathing air. This method is inaccurate insofar as the individual $CO_2$ values vary to a large extent, and therefore, a generally applicable threshold value cannot be determined. One tested person will not reach the threshold value at all, while with another person, in spite of exceeding this value, still no pure alveolar air will be present. In addition, a device which must determine two different gases and their concentrations is very expensive and sensitive (see U.S. Pat. No. 3,830,630).

Another arrangement for determining the gas component in the breathing air, namely, alcohol, measures this content at a definite instant which is determined by a timing control. This instant is set by the expiration of a predeterminable time interval starting within the period of exhalation. The rate of flow of the breathing air during this time interval must not drop below a predetermined minimum and, at the same time, the air must flow only in the direction of exhalation. Should these two conditions not be met, an error detector determines the invalidity of the measurement.

The predetermined time interval must insure that, at the instant of measurement, the tested person has already exhaled the air from the mouth and throat cavities and that the measuring device is now measuring the concentration of alcohol in the alveolar air. The expiration of the predetermined time interval is determined by the instant at which a minimum breathing air volume, preferably at least 80% of the total breathing air volume, is exhaled.

An integrator may integrate in time the rate of flow of the breathing air during the inhalation and exhalation and determine the expiration of the time interval from the minimum breathing air volume. Allegedly, such a design is independent of the body structure of the person to be tested. The disadvantage of this device is its very complicated construction since, for hygienic reasons, the volume measuring device must be provided twice, that is, in both the inhaling and the exhaling paths since it cannot be expected that the person to be tested inhale through a channel through which the previous person has exhaled.

A coincidence of the measured values of both volume measuring devices cannot be obtained with simple component parts and the same applies to an absolutely necessary checking. This method is not secure against measuring errors caused by a person who is unwilling to be tested. By an intentional shallow inhalation, for example, a too small breathing capacity may be simulated. Then, during the test, the minimum volume of breathing air, automatically adjusting, for example, at 80% of the total breathing volume, may come only from the mouth and throat cavities. Consequently, the alveolar air which is essential for an accurate measuring value will not be taken into account. (German Offenlegungsschrift No. 24 28 352).

Another known prior art method and device also requires the separation of the alveolar air from the mixed and commuting air to determine the exact content of the gas to be determined in the breathing air. The concern again is an arrangement for determining the alcohol content in the breathing air. To this end, during the tests, an infrared measuring device is provided which continuously measures the instantaneous alcohol concentration. The variation in time of the measured value is determined which is the measure for the rate of the alcohol concentration increase.

A measured value is passed to the indication only if the increase rate drops below a predetermined threshold value. This first condition results from the fact that with the dropping increase rate, the proportion of the commuting air from the mouth and throat cavities grows smaller and, upon dropping below the threshold value, only the alveolar air is present in the measuring channel of the device. As a further condition for passing the measured value to the indicator, the velocity of flow of the exhaled air which is determined by a flow meter must be above a predetermined value during a predetermined period of time up to the transmission of the measured value. This second condition ensures the correct carrying out of the test.

The alcohol concentration is measured by an infrared measuring device having a short response time and connected in the breathing air stream. A disadvantage of this device is that, due to the high resolution of the measuring value which is necessary for determining the increase rate, an expensive infrared measuring device is needed. The proportion of alveolar air cannot be separated for testing with simple, inexpensive, but slowly working alcohol measuring devices (German Offenlegungsschrift No. 26 10 578).

SUMMARY OF THE INVENTION

The present invention is accordingly directed to a simple and reliable method and device which ensures that only the alveolar air proportion of the breathing air is involved in the testing.

In accordance with the inventive method, the alveolar proportion or part of the breathing air is separated from the remainder by measuring the temperature of variation or change in the air which is passed through a passage and when the change drops below a predetermined threshold value, directing it into a measuring chamber. When the alveolar air is in the measuring chamber, a sensor device is used to determine the proportion of the desired gas component.

The method in accordance with the invention utilizes the fact that the temperature of the exhaled air is a function of the exhaled volume. The temperature attains a constant value or level simultaneously with the beginning of the exhalation of the alveolar air proportion. At that time, the increase rate of the temperature dropped to about zero. Measurements of temperature differences from measuring point to measuring point are simple prior art, provided that the temperature is measured continuously by means of a miniature temperature feeler. The secure and, in this way, very simple separation of the mixed and commuting air from the alevolar air then makes it possible to advantageously use simple, even slow, and correspondingly inexpensive, gas measuring devices.

With the inventive possibility of delaying the passage of the alveolar air proportion through the provided measuring chamber, in special applications, such as for particularly sensitive measurements, the separation may be made still more pronounced by separating the alveolar air proportion and, thereby, the measuring sample from the mixed air proportion by a larger interval.

The apparatus for the device of the invention includes a breathing tube which has a passage for the breathing air with a first branch terminating in a first outlet controlled by a first outlet valve and a second branch passing through a measuring chamber which has a first control valve for regulating the air flow into the measuring chamber and a second valve at the outlet out of the chamber to ambience which further includes a temperature sensor arranged in the breathing passage for sensing the temperature of the air. The temperature which is sensed is passed through a comparator which compacts its variation with a threshold value and acts upon an AND-gate to regulate the various shutoff valves so as to accumulate the desired alveolar air in the measuring chamber. The measuring chamber contains a sensing device for sensing a desired gas constituent of only the alveolar air in the measuring chamber.

These features concern the simple and advantageous construction of the device which, however, in spite of that, ensures that only the alveolar air proportion of the breathing air is measured. The mixed air and commuting air proportions are securely separated in advance.

Accordingly, the device for determining and separating the alveolar air proportion of breathing air and thereafter measuring a proportion of the desired gas component thereof the invention is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawing and descriptive matter in which a preferred embodiment of the invention is illustrated.

BRIEF DESCRIPTION OF THE DRAWING

The only FIGURE of the drawing is a schematic, sectional view of a breathing tube for separating and determining the alveolar air proportion of breathing air, constructed in accordance with the invention.

DESCRIPTION OF THE PREFERRED EMBODIMENT

Referring to the drawing in particular, the invention embodied therein, comprises, a device for determining and separating the alveolar air proportion of a first breathing air from the remainder and, thereafter, measuring the proportion of a desired gas component of the alveolar breathing air which is separated and which includes a breathing tube or gas testing tube 1 for that purpose.

The person whose breath sample is to be tested blows into a breathing air tube or testing tube 1, which is heated to 40° C., for example, to avoid condensation. The tube has an inlet 1a and two outlets 1b and 1c. The outlets 1b and 1c may be opened or closed by means of respective controlled shutoff valves 6 and 7. The temperature of the exhaled air is continuously measured immediately after its entry into breathing air tube 1, by means of a miniature temperature feeler 2 having a satisfactorily small time constant.

Since the temperatures of the alveolar breathing air which are usualy about 34.5° C., may vary by ±2° C., the attaining of a definite temperature value is not taken as a criterion for the entry of the alveolar breathing air into the breathing air tube 1, but the variations or change of the exhaled air temperature detected by electronic differentiation in a threshold value comparator 3 are followed. As soon as these temperature variations or changes reach a value close to zero, which means that a "condition a" has been obtained, it is ensured that then only actual alveolar air flows past the miniature temperature feeler 2. By means of timing switch 13, to which the threshold value comparator 3 is applied through the AND-gate 11, the shutoff valve 6 is closed and, at the same time, shutoff valve 7 is opened. The alveolar air then flows into measuring chamber 8. The concentration of the tested gas in the alveolar air proportion is then measured by means of a sensor 9 of the breathing gas measuring device which is provided in measuring chamber 8.

The breathing gas measuring device itself may even work discontinuously. In order to obtain this during the opening of shutoff valve 7, breathing air tube 1 is already completely filled with alveolar air and a delay switch 10 may be connected between threshold value comparator 3 and AND-gate 11. By the signal coming from AND-gate 11, the timing switch 13 is actuated through which the shutoff valves 5, 6 and 7 are controlled.

The introduction of alveolar air into measuring chamber 8 is automatically stopped by the closing of shutoff valve 7, provided that the valve has been open for a period of time sufficient to carry out the measurement. However, when a further shutoff valve 5 is used, the measuring chamber 8, after being scavenged, is filled only with alveolar air. In such instance, timing switch 13 also closes shutoff valve 5. The filling of measuring chamber 8 with alveolar air may be indicated optically or acoustically by means of indicators 14 and 15.

To prevent an unintentional or, for example, during the test for alcohol in the breath, intentional invalidation of the measured values by discontinuous exhalation or reinhalation, the breathing air flow is monitored, which is termed "condition b". With a flow meter 4, which operates by means of a sensitive differential pressure switch 12, it is ensured that with the satisfied "condition a", shutoff valve 7 is opened only if a sufficient flow velocity and a small excess pressure relative to the atmosphere is present in breathing air tube 1.

For this purpose, the measured value from differential pressure switch 12 is applied to AND-gate 11. Valid concentration values are obtained only if during the whole time of the measuring operation, both the "condition a" and the "condition b" are continuously and simultaneously satisfied at AND-gate 11. Should this not be the case, an acoustical or optical warning is given by indicators 14 and 15. In this case, the person whose breath is being tested must again flow into the device.

While a specific embodiment of the invention has been shown and described in detail to illustrate the application of the principles of the invention, it will be understood that the invention may be embodied otherwise without departing from such principles.

What is claimed is:

1. A method of determining and separating the alveolar air of a person's exhaled air from the remainder of the exhaled air and thereafter measuring a concentration of a desired gas component of the separated alveolar air, comprising, conveying the exhaled air at a minimum velocity through a conduit, continuously measuring a temperature of the conveyed air as the temperature changes, and when the changes in the temperature which is measured drops below a predetermined threshold value for such changes, directing the air into a measuring chamber, and using a sensor device in the measuring chamber to determine the concentration of the desired gas component.

2. A method, as claimed in claim 1, including directing the exhaled air into the chamber only after a predetermined delay.

3. A device for determining and separating the alveolar air part of a person's breathing air from the remainder and thereafter measuring a proportion of a desired gas component thereof, comprising, a tube for breathing air having a passage therethrough for the passage of the breathing air with a first end with a main inlet passage portion and including a first branch connected to said main inlet passage portion and terminating in a first air outlet to ambience and a second branch connected to said main inlet passage portion and terminating in a second outlet to ambience, wall means defining a measuring chamber for alveolar air connected in said second branch portion, respective first and second shutoff valves in said first and second branch portions, a third shutoff valve between said main inlet passage portion and said measuring chamber, a temperature sensor in said main inlet passage portion for continuously sensing the temperature of the breathing air, a threshold valve comparator connected to said temperature sensor, an AND-gate connected to said comparator and to said first, second and third shutoff valves and being responsive to temperature variations in respect to a predetermined threshold value to operate said third valve to admit air through said second passage portion to said measuring chamber and to selectively open and close said first and second shutoff valves.

4. A device, as claimed in claim 3, including a timing switch connected to said second shutoff valve.

5. A device, as claimed in claim 3, including a delay switch connected between said threshold comparator and said AND-gate.

* * * * *